United States Patent [19]

Lundbäck

[11] Patent Number: 4,957,477
[45] Date of Patent: Sep. 18, 1990

[54] HEART ASSIST JACKET AND METHOD OF USING IT

[75] Inventor: Stig S. Lundbäck, Vaxholm, Sweden

[73] Assignee: Astra Tech AB, Stockholm, Sweden

[21] Appl. No.: 349,871

[22] Filed: May 9, 1989

Related U.S. Application Data

[63] Continuation of Ser. No. 55,302, May 22, 1987, abandoned.

[30] Foreign Application Priority Data

May 22, 1986 [SE] Sweden ................. 8602335

[51] Int. Cl.⁵ .................................... A61B 17/00
[52] U.S. Cl. .............................. 600/16; 600/37
[58] Field of Search ............. 128/64; 600/16, 17, 600/18, 37

[56] References Cited

U.S. PATENT DOCUMENTS

| | | | |
|---|---|---|---|
| 2,826,193 | 3/1958 | Vineberg | 128/64 |
| 3,919,722 | 11/1975 | Harmison | 623/3 |
| 4,536,893 | 8/1985 | Parravicini | 128/64 |
| 4,637,377 | 1/1987 | Loop | 600/37 |
| 4,690,134 | 9/1987 | Snyders | 128/64 |

FOREIGN PATENT DOCUMENTS 611617  6/1978  U.S.S.R. ................. 128/64

*Primary Examiner*—Kyle L. Howell
*Assistant Examiner*—Kennedy J. Schaetzle
*Attorney, Agent, or Firm*—White & Case

[57] ABSTRACT

A heart assist device for insertion into the thoracic cavity of a patient comprises a double-walled jacket (10) adapted to enclose at least the ventricular portion of the heart (H), at least the inner wall (11) of the jacket being pliable to be able to engage the outer surface of the heart and move together with the walls of the heart, and the interspace (13) between the inner and outer walls of the jacket being closed and filled with a fluid which is easily displaceable within the interspace.

8 Claims, 2 Drawing Sheets

HEART ASSIST JACKET AND METHOD OF USING IT

This application is a continuation of application Ser. No. 07/055,302, filed on May 22, 1987, now abandoned.

FIELD OF THE INVENTION

This invention relates to heart assist devices for intracorporal use. More particularly, the invention concerns a heart assist device for insertion into the thoracic cavity of a patient to enclose at least the ventricular portion of the patient's heart and a method for therapeutic treatment using such device.

BACKGROUND OF THE INVENTION

As asserted in Lundbäck S., "Cardiac Pumping and Function of the Ventricular Septum", Stockholm, 1986, the pumping and regulation of the human heart take place in a manner which is at variance with the prevalent view.

According to the cited publication, the healthY heart performs its pumping action without substantially changing its outer shape and volume.

More particularly, during ventricular systole (the active, expulsive phase of the heart cycle) the so-called valve plane, that is, the plane containing the atrioventricular heart valves, is drawn towards the heart apex and forces the blood contained in the ventricles into the pulmonic and systemic circulation, and at the same time blood is drawn into the atria as a consequence of the movement of the valve plane.

During ventricular diastole, the phase of the heart cycle in which the heart muscle is relaxed, the valve plane is returned to the initial position under the influence of the momentum which is imparted to the inflowing blood as a consequence of the downward movement of the valve plane during ventricular systole.

As is also asserted in the publication (on the basis of the finding that the outer volume and shape of the heart are substantially constant over the heart cycle), the ability of the heart to change the relative volumetric capacities of the right and left ventricles is attributable only to the common ventricular wall, the ventricular septum, namely by virtue of its flexibility in the relaxed state of the heart. During ventricular systole the ventricular septum together with the rest of the left ventricular musculature always assumes a circular cross-sectional configuration and takes a distinct position independentlY of its shape and position during diastole. This is so, because during ventricular systole the pressure in the left ventricle is always higher than the pressure in the right ventricle. If the configuration and position of the ventricular septum during diastole, the relaxed state, are different from the configuration and position during systole, the active state, the ventricular septum, acting like a diaphragm pump, therefore provides an increased stroke volume for one ventricle and a correspondingly reduced stroke volume for the other ventricle. In this way, the ventricular septum accomplishes a double-acting regulation to maintain the balance between the two branches of the circulatory system (the pulmonary circulation and the systemic circulation).

Many advantages are attributable to this mode of work and regulation of the heart, and the realization of this mode of operation answers questions concerning the physiology of the heart which have not until now been answered consistently.

For the heart to be able to perform its pumping and regulation with constant outer shape and volume, it is necessary that the muscular power of the ventricular septum is not substantially reduced in comparison with the rest of the musculature of the left ventricle, as may be the case for example when an infarction has been inflicted on the ventricular septum. As a consequence of such a damage, the ventricular septum during ventricular systole becomes unable both to withstand the pressure in the left ventricle and to perform a proper regulatory function. Therefore, the ventricular septum will yield to the pressure in the left ventricle and provide an abnormally increased stroke volume on the right side of the heart and a corresponding reduction of the stroke volume on the left side. Consequently, more blood is pumped into the pulmonary circulation than into the systemic circulation. This, in turn, because of the impaired or lost regulatory function of the ventricular septum, causes an accumulation of blood in the lungs resulting in pulmonary edema. Such a course of events is life-threatening.

However, experiments carried out on animals with the heart working in the opened thorax, that is, surrounded by air, have shown that simulated infarctions inflicted on the ventricular septum do not have the disastrous consequences indicated above.

Under the conditions in which the experiments were carried out, the heart works as a different type of displacement pump, namely, as a pump doing its work with varying outer volume and shape. This also means that the ventricles under diastole can change their volumes not only as a result of displacement of the ventricular septum, but also as a result of displacement of the rest of the ventricular walls. During systole the ventricles can therefore provide different stroke volumes without influencing one another as much. This type of pumping and regulation is consistent with the prevalent view of the way the heart works when it is enclosed in the body.

DESCRIPTION OF THE INVENTION

Underlying the present invention is the realization that the heart when enclosed in the body works in a way that is different from the way it works when it is exposed, that is, when it is surrounded by air, and that in the first-mentioned case heavy infarctions in the ventricular septum may lead to disastrous circulatory disorders while simulated infarctions in the ventricular septum of a heart surrounded by air do not cause fatal circulatory disorders.

According to the invention there is provided a heart assist device for insertion into the thoracic cavity of a patient and comprising a jacket for enclosing at least the ventricular portion of the patient's heart, the heart assist device having the characterising features set forth in claim 1.

As explained in greater detail hereinafter, the device according to the invention is used to provide a compliant support for at least the ventricular portion of the heart within the thoracic cavity. Because of this compliant support the heart when enclosed in the patient's thoracic cavity can work with the outer shape and volume changing rhythmically with the heart beats.

Principally, the device according to the invention is useful for therapeutic purposes in cases where the ventricular septum of a patient's heart has suffered an infarction and is therefore unable to perform its normal regulatory function maintaining the balance between the pulmonary circulation and the systemic circulation.

In accordance with the invention, the jacket allows that portion of the wall of the left ventricle which is engaged by the inner wall of the jacket to move outwardly in response to increasing diastolic filling pressure in the left ventricle. It is, therefore, possible for the left ventricle to increase its stroke volume not only by movement of the ventricular septum towards the right ventricle but also by an outward movement of the rest of the ventricular wall.

The outward movement of the wall of the left ventricle and the resulting increased filling and stroke volumes cause a movement of the inner wall of the jacket toward the outer wall, which is rather firmly supported by the adjacent organs of the thorax, that is, the parts of the patient's body which define the cavity accommodating the heart. As a consequence, the fluid is displaced within the jacket and causes a decrease of the filling and stroke volumes of the right ventricle by, for example, an inward movement of the part of the wall of the right ventricle which is engaged by the jacket. This interaction contributes to balancing of the outflows from the ventricles.

In other words, in accordance with the invention the regulatory function of the ventricular septum is shifted to that portion of the wall of the left ventricle which is engaged by the inner wall of the jacket.

Preferably, the fluid enclosed in the jacket, or at least a portion of the fluid, is compressible. In order that fluid may be added or removed, one end of a flexible conduit may be connected to the interspace, the other end being provided with a self-sealing terminal through which fluid may be supplied to the jacket or removed therefrom by means of a syringe. Suitably, the terminal is positioned under the patient's skin.

It is also within the scope of the invention to provide the jacket with an expansion vessel which communicates with the interspace of the jacket and may include means for controlling the fluid pressure in the interspace.

A jacket that encloses only the ventricular part of the heart may be sufficient for practical purposes and has the advantages of being structurally simple and of being easy to apply to the heart. If the jacket is adapted to enclose substantially the entire heart, functional advantages can be attained. For example, the variations of the volume of the part of the jacket which encloses the ventricular portion of the heart can be utilized to bring about variations of the volumes of the atria of the heart in phase opposition to the variations of the volumes of the ventricles.

The jacket may be a unitary or one-piece structure which is foldable to enclose the ventricular portion only or the entire heart. Alternatively, it may be made in two or more separate parts which can be assembled around the heart.

If the jacket is designed to enclose the entire heart, the edges of the jacket suitably have recesses at appropriate locations so that lead-through passages for the blood vessels leading to and from the heart can be formed.

If the jacket is made in two or more separate parts, the closed spaces between the walls of the parts may be placed in fluid flow communication with one another so that the fluid can be moved back and forth between the parts.

When the jacket is inserted into the body it may be appropriate to strengthen the ventricular septum by a suitable material. Advantageously, this is done on the side facing the right ventricle, so that any emboli caused by the strenghtening material are prevented from entering the systemic circulation.

The appended drawings diagrammatically show two embodiments of the heart assist device according to the invention and the use of the device for supporting a human heart in situ.

Figure 1:
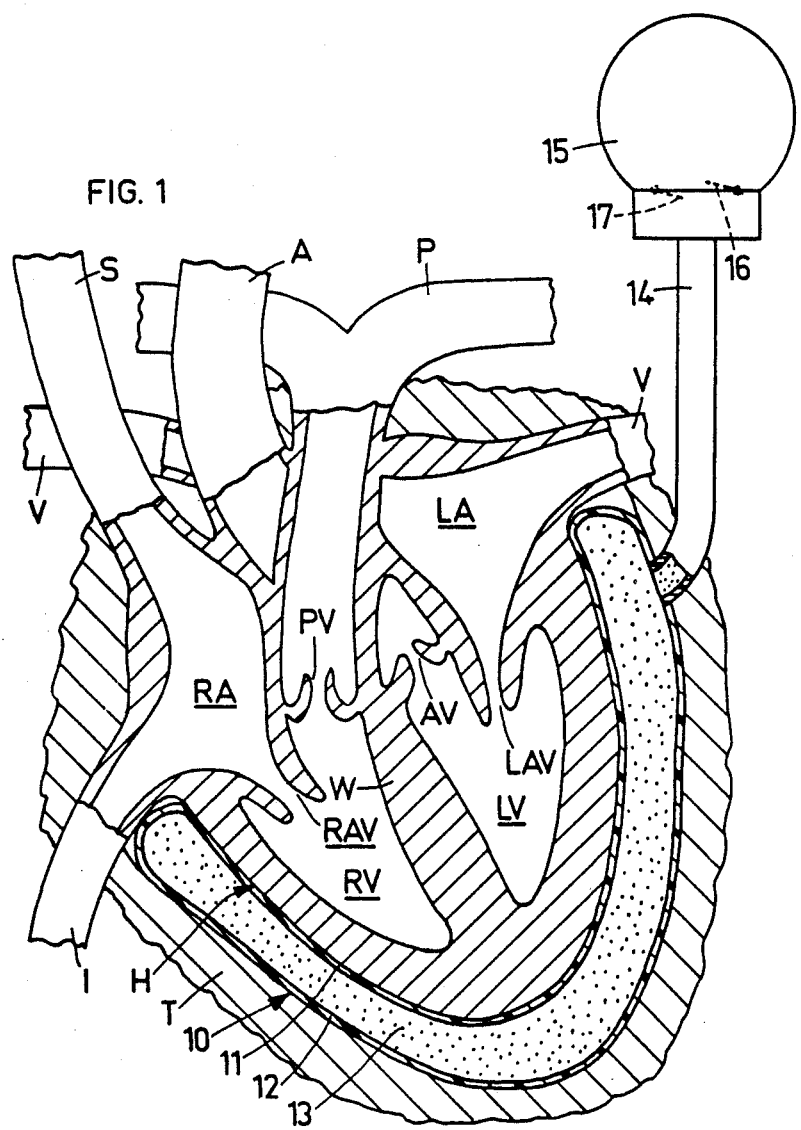
FIG. 1 is a cross-sectional view showing an embodiment in which the jacket of the device encloses only the ventricular portion of the heart.
Figure 2:
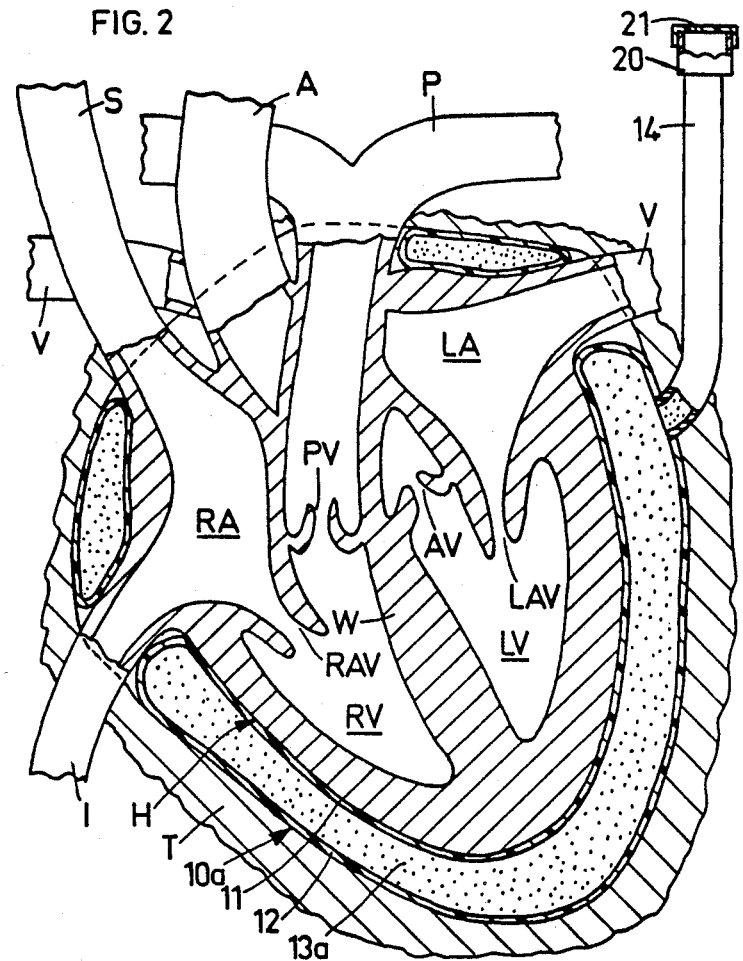
FIG. 2 is a similar cross-sectional view showing an embodiment in which the jacket of the device encloses the entire heart and has openings or lead-through passages for the blood vessels leading to and from the heart.

Referring to the drawings, and FIGS. 1 and 2 in particular, the wall of the thoracic cavity accommodating a patient's heart H is shown at T. Also shown are the superior vena cava S and the inferior vena cava I, both opening into the right atrium RA which in turn opens into the right ventricle RV through the right atrioventricular valve RAV; the pulmonary artery P receiving blood from the right ventricle RV through the pulmonary valve PV; the pulmonary veins V opening into the left atrium LA which in turn opens into the left ventricle LV through the left atrioventricular valve LAV; the aorta A receiving blood from the left ventricle LV through the aortic valve AV; and the ventricular septum W separating the two ventricles.

Inserted between the thoracic cavity wall T and the heart H is the bladder-like jacket of the heart assist device of the present invention. This jacket is designated 10 in FIG. 1 and 10a in FIGS. 2 and 3.

Referring now to FIG. 1, the jacket 10 is in the shape of a bowl the internal shape of which corresponds to the shape of the ventricular portion of the heart H. The inner wall 11 is made of a thin, pliable sheet of biocompatible, preferably wholly or partly radiopaque material so that it can readily conform to and engage snugly the outer side of the ventricular heart portion and adopt the shape thereof. Thus, the inner wall 11 is capable of moving together with the outer wall of the ventricular heart portion.

Advantageously, the outer wall 12 also consists of a thin pliable sheet of biocompatible material so that when the jacket 10 is inserted into the thoracic cavity the outer wall 12 can conform to the shape of the surrounding thoracic cavity wall T.

The hermetically closed interspace 13 between the inner wall 11 and the outer wall 12 is filled with a suitable fluid, marked by dotting, which may be a gas or a liquid or partly a gas and partly a liquid. Preferably, at least a portion of the fluid is a gas.

The fluid keeps the inner wall 11 and the outer wall 12 spaced apart, at least over the major portion of the area over which the inner Wall 11 engages the heart H, so that the outer walls of the ventricles RV, LV can move towards and away from the outer jacket wall 12 and, thus, the thoracic cavity wall T.

Unless the material of the inner and outer walls 11, 12 itself possesses suitable low-friction properties, a suitable lubricating agent in the form of a liquid or liquid suspension should form part of the interspace fluid, or the surfaces of the inner and outer walls 11, 12 should be coated with a suitable lubricant, so that the inner wall 11 can easily slide on the outer wall 12 in case the walls should contact one another in use of the jacket.

Connected with the otherwise hermetically sealed jacket 10 is a flexible conduit 14 through which the interspace 13 communicates with a hermetically sealed, implantable expansion vessel 15. This expansion vessel is shown as having inlet and outlet valves 16 and 17, respectively, which are in the form of non-return valves and set to open in response to a predetermined pressure differential between the expansion vessel and the interspace 13. The valves are not indispensable, however.

As shown in FIG. 1, the expansion vessel 15 comprises a bag or bladder which can be compressed or allowed to expand for changing the volume thereof.

Because the ventricular portion of the heart is supported compliantly (resiliently if at least a portion of the fluid is compressible) by the inner wall 11, the ventricular walls of the heart H may move without substantial restraint so that the heart can perform its pumping action in the manner explained above, that is, so that the ventricles RV, LV can interact not only through the intermediary of the ventricular septum W but also through the rest of the ventricular walls, as is necessary in the event of a damage to the ventricular septum W in order that the regulatory function maY be maintained. The expansion vessel 15 is dimensioned such that the change of the volume of the interspace 13 does not result in undue pressure changes.

Figure 3:
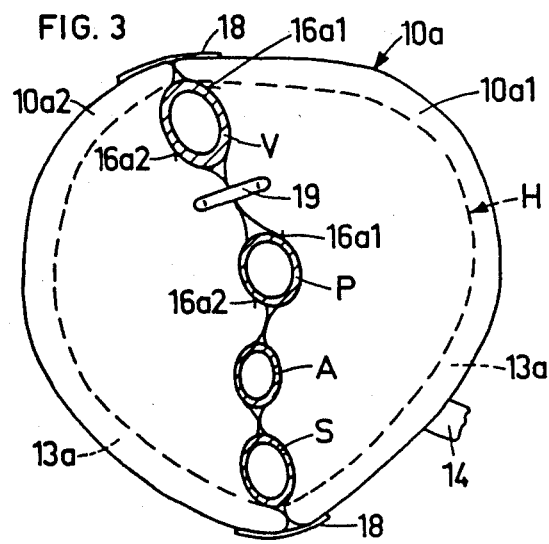
FIG. 3 is a view from above of the embodiment of FIG. 2 and illustrates division of the jacket into two halves or parts which are assembled to enclose the heart between them.

The jacket 10a of FIGS. 2 and 3 differs from that of FIG. 1 in that it encloses the entire heart H like a capsule. To facilitate the application of the jacket to the heart H, the jacket is made in two parts 10a1, 10a2, which can be folded or assembled around the heart and interconnected by suitable fasteners 18 as shown in FIG. 3. The two parts are formed with recesses 16a1, 16a2 at those edges which are intended to be in engagement with, or positioned adjacent to, one another when the parts are fitted around the heart. The recesses are located and shaped such that they can form lead-through passages for the superior vena cava S, the inferior vena cava 1 (not shown), the pulmonary artery P, the pulmonary veins V and the aorta A.

The interspaces 13a of the different parts are hermetically sealed but communicate, or can be made to communicate, with one another through suitable conduit means as indicated at 19 so that the fluid can be moved between the parts.

As is evident from FIG. 2, inward movement of the outer walls of the ventricles RV, LV will increase the volume of the portion of the jacket 10a which engages the ventricles and cause a corresponding reduction of the volume of the portion of the jacket which engages the outer walls of the atria RA, LA. This reduction of volume and the resulting displacement of the fluid in the jacket causes an outward movement of the outer walls of the atria, that is, an increase of the volumetric capacity of the atria. Similarly, outward movement of the outer walls of the ventricles causes inward movement of the outer walls of the atria. Such movements in phase opposition improve the pumping of the heart.

In the embodiment of FIG. 2, no expansion vessel is provided. Instead, the outer end of the flexible conduit 14 is provided with an implantable, terminal device 20 having a self-sealing puncturable diaphragm 21 through which fluid may be introduced into or removed from the interspaces 13a when required, using a syringe, the needle of which is caused to penetrate the diaphragm. Naturally, an expansion vessel corresponding to the expansion vessel 15 of FIG. 1 may be provided instead of or in addition to the terminal device 20. Similarly, in the embodiment of FIG. 1 a terminal device corresponding to the terminal device 20 may be provided in addition to or instead of the expansion vessel 15.

In a third embodiment, not shown, the jacket likewise encloses the entire heart. In this embodiment the jacket comprises a lower part identical to the jacket 10 in FIG. 1 (with or without the expansion vessel 15) and an upper part adapted to enclose the upper or atrial portion of the heart. The upper jacket part is made up of two subparts or segments to facilitate the application to the heart so that when viewed from above it resembles the portion of the jacket 10a shown in FIG. 3. A cross-sectional view of the third embodiment would be more or less identical to the illustration given in FIG. 2.

If desired, the upper and lower parts of the third embodiment can be provided with interconnecting conduits through which the interiors of the parts communicate. Such communication can be dispensed with, however.

It should be noted that the device according to the invention in all embodiments thereof defines a hermetically sealed system within which the fluid is displaceable and that in use of the device for maintaining the regulatory function which is normally accomplished by the ventricular septum but shifted to other parts of the ventricular walls in the event of an infarction in the ventricular septum, no force is applied to the heart from outside the body through the intermediary of the jacket, that is, the device is passive. Thus the device according to the invention is to be distinguished from devices which are used to apply an external force to the heart in order to compress it, e.g., for the purpose of reducing the volumes of the ventricles or for stimulating the heart muscle.

I claim:

1. A passive heart assist device for insertion into the thoracic cavity of a patient between the thoracic wall and the heart comprising:
   a jacket having relatively moveable, connected inner and outer walls, wherein said inner wall is formed of pliable material and is adapted to fit snugly around at least the ventricular portion of the heart over the left and right ventricles; wherein said walls define a fluid-containing innerspace including a left ventricle portion and a right ventricle portion; wherein said portions are in fluid communication with one another; and means for maintaining a volume of fluid in said innerspace at all times, wherein said fluid is displaceable from one portion to the other in response to movement of one of the ventricles toward said outer wall thereby to enable the stroke volumes of the ventricles to vary as the heart beats.

2. A hear assist device as claimed in claim 1, wherein the inner wall of said jacket is adapted to fit snugly around substantially the entire heart and the jacket includes recesses defining openings for the veins and arteries leading to and from the heart, and further comprising means connecting portions of the jacket on opposite sides of the openings to each other.

3. A heart assist device as claimed in claim 2, wherein said jacket consists of a plurality of parts, each having relatively moveable, connected inner and outer walls and each part defining a part of said innerspace formed by its inner and outer walls, the inner walls of each jacket part consisting of pliable material and further comprising means joining the jacket parts to each other such that the parts in combination are adapted to fit snugly around substantially the entire heart and means for providing fluid communication between said parts of the jacket.

4. A heart assist device as claimed in claim 1, and further comprising an expansion reservoir and conduit means providing fluid communication between the jacket and the expansion reservoir.

5. A heart assist device as claimed in claim 1, wherein said fluid is a compressible fluid.

6. A heart assist device as claimed in claim 1, further comprising a conduit having one end in fluid communications with said jacket and having an opposite end covered by a self-sealing membrane through which fluid may be supplied to and removed from said jacket.

7. A method of supporting a patient's heart in vivo comprising the steps of:

providing a jacket having relatively moveable, connected inner and outer walls, wherein said inner wall is formed of pliable material and is adapted to fit snugly around at least the ventricular portion of the heart over the left and right ventricles; wherein said walls define a fluid-containing innerspace including a left ventricle portion and a right ventricle portion; wherein said portions are in fluid communication with one another;

inserting said jacket into the thoracic cavity of a patient between the thoracic wall and the heart such that said left ventricle portion fits over said left ventricle and said right ventricle portions fit over said right ventricle; and maintaining a volume of fluid in said innerspace at all times, wherein said fluid is displaced from one portion to the other in response to movement of one of the ventricles toward said outer wall with the jacket thus functioning passively to enable the stroke volumes of the ventricles to vary as the hear beats.

8. A method as claimed in claim 7 comprising the additional step of:

adjusting the amount of fluid in said volume to control the degree of responsiveness of said inner wall to movement of said heart.

* * * * *

UNITED STATES PATENT AND TRADEMARK OFFICE
CERTIFICATE OF CORRECTION

PATENT NO. : 4,957,477

DATED : September 18, 1990

INVENTOR(S) : Stig S. Lundback

It is certified that error appears in the above-identified patent and that said Letters Patent is hereby corrected as shown below:

col. 1, line 22, "health Y" should read --healthy--;

col. 1, line 50, independentlY" should read --independently--;

col. 3, line 56, "onlY" should read --only--;

col. 5, line 29, "maY" should read --may--;

col. 6, line 67, claim 3, "as claimed in claim 2," should read --as claimed in claim 1--;

col. 7, line 3, claim 3, "inner walls" should read --inner wall--;

col. 7, lines 17-18, claim 6, "communications" should read --communication--;

col. 8, line 18, claim 7, "hear" should read --heart--;

Signed and Sealed this

Twenty-eighth Day of April, 1992

*Attest:*

HARRY F. MANBECK, JR.

*Attesting Officer*      *Commissioner of Patents and Trademarks*